United States Patent [19]

Bowe et al.

[11] Patent Number: 5,335,656
[45] Date of Patent: Aug. 9, 1994

[54] METHOD AND APPARATUS FOR INHALATION OF TREATING GAS AND SAMPLING OF EXHALED GAS FOR QUANTITATIVE ANALYSIS

[75] Inventors: Edwin A. Bowe; E. F. Klein, Jr., both of Columbia, S.C.; Philip G. Boysen, Gainesville, Fla.

[73] Assignee: Salter Laboratories, Arvin, Calif.

[21] Appl. No.: 964,070

[22] Filed: Oct. 21, 1992

Related U.S. Application Data

[63] Continuation of Ser. No. 683,885, Apr. 11, 1991, abandoned, which is a continuation of Ser. No. 458,653, Dec. 15, 1989, abandoned, which is a continuation of Ser. No. 544,501, Jun. 27, 1990, abandoned, which is a continuation of Ser. No. 181,814, Apr. 15, 1988, abandoned.

[51] Int. Cl.⁵ .............................................. A61M 15/08
[52] U.S. Cl. ............................ 128/207.18; 128/206.11; 128/719
[58] Field of Search .................... 128/204.23, 204.26, 128/205.19, 207.18, 206.11, 912, DIG. 26, 719

[56] References Cited

U.S. PATENT DOCUMENTS

| | | | |
|---|---|---|---|
| 2,208,633 | 7/1940 | Heidbrink | 128/203.28 |
| 2,750,938 | 1/1956 | Bier | 128/716 |
| 3,513,844 | 1/1970 | Smith | 128/207.18 |
| 4,054,133 | 10/1977 | Myers | 128/207.18 |
| 4,106,505 | 8/1978 | Suller et al. | 128/207.18 |
| 4,120,300 | 10/1978 | Tiep | 128/204.24 |
| 4,446,869 | 5/1984 | Knodle | 128/716 |
| 4,484,578 | 11/1984 | Durkan | 128/204.24 |
| 4,602,644 | 7/1986 | DiBenedett et al. | 128/207.18 |
| 4,619,269 | 10/1986 | Cutler et al. | 128/719 |
| 4,686,975 | 8/1987 | Naimen et al. | 128/204.23 |
| 4,790,308 | 12/1988 | Weichselbaum | 128/207.18 |
| 4,821,736 | 4/1989 | Walson | 128/207.18 |
| 4,856,531 | 8/1989 | Merilainen | 128/719 |
| 4,958,075 | 9/1990 | Moie et al. | 128/719 |
| 4,989,599 | 2/1991 | Carter | 128/207.18 |
| 5,005,571 | 4/1991 | Dietz | 128/205.25 |
| 5,046,691 | 9/1991 | Derrick | 128/200.24 |

FOREIGN PATENT DOCUMENTS

8909565 10/1989 PCT Int'l Appl. .
WO8401293 4/1984 World Int. Prop. O. .

OTHER PUBLICATIONS

"Mass Spectrometer Monitoring of Patients with Regional Anesthesia", by Ibarra et al., Anesthesiology 63:572–573, 1985.

*Primary Examiner*—J. Reed Fisher
*Assistant Examiner*—Aaron J. Lewis
*Attorney, Agent, or Firm*—Shoemaker & Mattare, Ltd.

[57] ABSTRACT

A nasal cannulae is described for insufflating a treating gas into one nostril and measuring at least one gaseous component of exhaled breath in the other nostril of a living body. The cannulae includes a wall member co-operating with a hollow body of the cannulae to define inhalation and exhalation manifolds and sealingly engaging the hollow body to provide a gas-tight seal for positively preventing fluid communication between these manifolds. A hollow nasal prong communicates with each manifold and is positioned and shaped to be received in a corresponding nostril. The wall member may be integrally molded with the body of the cannulae when it is made or a conventional cannulae may be modified by insertion of a wall member to create separate manifolds. The nasal prongs may have the same or different lengths.

3 Claims, 6 Drawing Sheets

METHOD AND APPARATUS FOR INHALATION OF TREATING GAS AND SAMPLING OF EXHALED GAS FOR QUANTITATIVE ANALYSIS

This application is a continuation of application Ser. No. 07/683,885 filed Apr. 11, 1991 now abandoned, which is a continuation of Ser. No. 07/458,653 filed Dec. 15, 1989 now abandoned, which is a continuation of Ser. No. 07/544,501 filed Jun. 27, 1990 now abandoned, which is a continuation of Ser. No. 07/181,814 filed Apr. 15, 1988 now abandoned.

TECHNICAL FIELD

The present invention relates to medical treatment and monitoring of a living body, and more particularly to an apparatus and method for insufflating a treating gas into the inhalation of a living body and sampling the exhalation of the living body for quantitative analysis of at least one gaseous component thereof.

BACKGROUND OF THE INVENTION

When a living body, such as a human patient, is sick or being operated upon, it is often necessary to supplement the body's inhalation with a treating gas, such as oxygen or a gaseous anesthetic. In these instances, an accurate quantitative determination of the amount of at least one gaseous component, such as carbon dioxide, in the blood passing through the pulmonary alveoli of the living body is highly desirable. In intensive care situations or under a regional or general anesthetic, an accurate determination of the composition of the breathing gas in the pulmonary alveoli allows bodily functions of a patient to be more readily supervised and treatment of the patient more favorably adapted to the state of those functions. Accurate measurements of at least one gaseous component in the exhalation of a living body also may help improve related diagnostic methods for determining bodily conditions. Measuring the concentration of at least one gaseous component in exhaled breathing gas may be conducted continuously to provide relatively short response times and to enable rapid alterations in an ongoing medical procedure, thereby preventing adverse effects or damage to the living body.

One area of particular interest is the monitoring of end-tidal carbon dioxide, which is the partial pressure of the carbon dioxide component of exhaled gas at the end of exhalation in a spontaneously breathing patient. The quantitative monitoring of end-tidal carbon dioxide in spontaneously breathing patients who are unintubated (those not requiring intubation with an endotracheal tube) would be particularly useful for those unintubated patients who while awake are being treated with supplemental oxygen administration and are receiving regional or local anesthesia or are in a recovery room during emergence from residual general anesthesia. However, previously proposed devices for combined sampling and oxygen administration, while allowing general qualitative detection of carbon dioxide in exhaled breathing gas (and therefore a determination of apnea), have not allowed a quantitative analysis of the carbon dioxide which correlates adequately with the actual amount of this gaseous component in the arterial blood. Consequently, it has not been possible heretofore by breath sampling from an awake patient receiving supplemental oxygen to quantitatively determine the magnitude of respiratory depression occurring as a result of local or regional anesthesia or intravenous sedation.

Prior techniques for insufflating a treating gas into the breathing gas of a patient and simultaneously measuring at least one gaseous component of the exhalation of the patient have involved withdrawing a breathing gas sample through a chamber or conduit receiving both exhaled gas and at least some amount of the insufflated treating gas. For example, the breathing gas sample has been withdrawn from an oxygen mask over the patient's nose and mouth as illustrated by the article of Huntington, et al., in *Anesthesiology* 65:565–566, 1986. Huntington, et al., inserted an ordinary IV catheter through one of the side ports of a disposable oxygen mask to a point close to the patient's nose and connected it to the sampling tube of a mass spectrometer. According to the authors, the technique was "as satisfactory, but simpler" in comparison with both the Iberra, et al., and the Norman, et al., devices described below.

In an article by Iberra and Lees in *Anesthesiology* 63:572–573, 1985, there is described a device wherein the sampling catheter of a mass spectrometer is inserted into one prong of the pair of prongs of a conventional nasal cannulae. Although the authors suggest that a sampling catheter so arranged may be used to monitor ventilatory exchange during regional anesthesia, our attempts to use this arrangement for quantitative measurements were unsuccessful because of excessive differences between measured values of end-tidal carbon dioxide and measured values of arterial carbon dioxide.

It had been previously recognized that the differences between arterial carbon dioxide values and end-tidal carbon dioxide values as measured with the Iberra and Lees arrangement were too excessive and erratic to provide a quantitative indication of arterial carbon dioxide. This problem led other researchers in the field, such as Huntington, et al., supra, to conclude that the Iberra and Lees arrangement was unsatisfactory and to try other approaches to achieving a device for quantitative measurements of end-tidal carbon dioxide in unintubated patients while administering supplemental oxygen. Also, in a subsequent article in *Anesthesiology* 64:664, 1986, Norman, et al., suggest as an alternative to the "unsatisfactory" Iberra and Lees arrangement, that the tip of a sampling catheter (with the proximal connector removed as in Iberra and Lees) be sutured 1 cm. from the pharyngeal opening of a conventional nasal airway. A nasal airway is highly uncomfortable because it completely fills and blocks a nasal passage of the patient. Therefore, as is noted in this article, insertion of the airway requires a "lubricant containing local anesthetic". Although the modified nasal airway device produced a "satisfactory ET $CO_2$ curve" more consistently than the Iberra and Lees arrangement, "neither method is as reliable as monitoring ET $CO_2$ via an endotracheal tube". In addition, there is no provision in the Norman, et al., device for insufflating a treating gas such as oxygen.

There is therefore a real need in the art for an insufflating and sampling apparatus having the combined advantageous of insufflating a treating gas into an awake patient and sampling a portion of the patient's exhaled breathing gas in a manner providing a quantitative correlation between measured levels of a gaseous component in the breathing gas and measured levels of the same component in the patient's arterial blood. Neither the Iberra, et al., device apparently nor the Huntington, et al., device fulfill this need because the differences between measured values of end-tidal carbon dioxide in breath samples from these devices and measured values of arterial carbon dioxide are too excessive and erratic to provide a quantitative correlation. The Norman, et al., device apparently also has this deficiency and, in addition, has no provision for insufflating a treating gas simultaneously with sampling of exhaled gas. It is therefore a purpose of the present invention to fulfill the foregoing need.

SUMMARY OF THE INVENTION

The present invention overcomes the foregoing deficiencies of the prior art and provides a combined administration and sampling device for treating gas insufflation into an awake patient and simultaneous sampling giving accurate and reliable quantitative measurements of a gaseous component in exhaled breathing gas. Thus, the nasal cannulae of the present invention is capable of administering oxygen to an awake patient while providing measurements of end-tidal carbon dioxide which are quantitatively equivalent to measurements of end-tidal carbon dioxide obtained by sampling via an endotracheal tube inserted into the trachea (intubation) of a sedated or anesthetized patient. The quantitative measurements available with the present invention thus have a direct correspondence to the actual levels of arterial carbon dioxide. The sampling and analysis regimen may be carried out alone or simultaneously with a regimen for insufflating a treating gas, such as oxygen, into the natural air being inhaled by the patient.

It is believed that the spurious and unreliable results experienced in prior art attempts at such quantitative measurements may be due at least in part to contamination of the exhaled gas sample with the treating gas. Therefore, an object of the present invention is to prevent substantially any leakage or backflow of treating gas into the sampled gas flowpath. This and other objects and advantages are achieved by the method and apparatus of the invention wherein an elongated hollow body, such as a conventional cannulae, is divided into separate inhalation and exhalation manifolds by a substantially impermeable wall member which sealingly engages a cooperating wall of the hollow body and/or a hollow extension thereof, such as a nasal prong, to provide a continuous gas-tight seal between the two manifolds. This apparatus, which thereby has positive sealing means between the flowpath of insufflated treating gas and the flowpath for sampling exhaled breathing gas, provides quantitative measurements of a gaseous component of the exhaled gas which differ only by relatively small and medically insignificant amounts from direct measurements of the gaseous component in corresponding arterial blood samples. The invention thus provides an accurate, consistent and therefore reliable indication of the actual amounts of one or more gaseous component in the arterial blood of a patient.

The wall member of the invention may take different forms, and these may suggest other forms to those skilled in the art. If made as a new product, the invention preferably is in the form of a nasal cannulae having an internal septum located midway between a pair of nasal prongs and extending transversely to sealingly divide the interior of the hollow main body into two entirely separate chambers, one serving as a treating gas manifold in fluid communication with a corresponding nasal prong and the other serving as a sampling gas manifold in fluid communication with the other nasal prong. Although the internal septum is preferably integrally molded with the wall of the main body, the necessary sealing engagement between the septum and the main body may be provided by some other form of adhesion, such as an adhesive composition or a solvent or sonic weld. In all of these alternatives, the sealing means is such that the entire periphery of the septum sealingly engages an abutting wall of the main body to form a continuous gas-tight seal isolating the treating gas manifold from the sampling gas manifold.

As an alternative to a new product, a conventional nasal cannulae may be modified so as to provide a sampling manifold positively sealed from a treating gas manifold. In this embodiment, the conventional cannulae selected is made of a relatively flexible and elastic plastic material and an aperture is cut or pierced in the tubular main body of the cannulae at the base of one of the nasal prongs. There is then inserted through the aperture and into the corresponding nasal prong a nozzle-like piece of substantially more rigid material than the material of the cannulae. The nozzle has a diameter substantially larger than that of either the aperture or the corresponding nasal prong so that the nozzle stretches both the elastic material around the aperture and the elastic material of the nasal prong, thereby causing the material of the cannulae in these areas to sealingly engage the abutting exterior surface of the inserted nozzle. The interior of the inserted nozzle may then serve as either the inhalation or exhalation manifold and the exterior of the nozzle cooperates with the wall of the tubular main body cannulae to define the other manifold.

The inserted nozzle piece preferably includes an outer flange which may be engaged by the threads or other coupling means of a connector for connecting the nozzle to a flexible conduit for either supplying treating gas to the nozzle manifold or withdrawing a sample of exhalation gas from the nozzle manifold. Where the nasal prongs are tapered, the main body portion of the nozzle is preferably also tapered by a generally corresponding amount. It is also most preferable that the nozzle piece have an external diameter greater than the internal diameter of the corresponding prong passage into which it is inserted substantially throughout the length of the prong passage, such that positive sealing engagement exists along substantially the full extent of the portion of the nozzle inserted within the prong passage. The length of this sealing engagement helps to reduce the likelihood of a seal rupture due to gas pressure or manipulation of the modified cannulae. While substantially full length engagement is most preferable, the invention contemplates sealing engagement between the outer surface of the nozzle and the inner surface of the prong wall over at least a substantial portion of the prong length and preferably a majority of the prong length.

The apparatus of the invention further contemplates a first hollow prong in fluid communication with the inhalation manifold, and a second hollow prong in fluid communication with the exhalation manifold. The first hollow prong is adapted to be received in a first nasal passage of a nose of a living body, such as a human body, for insufflating a treating gas, such as oxygen, into the inhaled breath of the living body. The second hollow prong is adapted to be received in a second nasal passage of the nose for withdrawing a portion of the exhaled breath of the living body as a gas sample to be quantitatively analyzed. A gas sample conveying means provides substantially all of the withdrawn gas sample to a means for quantitatively measuring the amount of at least one gaseous component, such as carbon dioxide, of the gas sample. This withdrawn portion is sufficiently isolated from the insufflated treating gas for the amount of the gaseous component in the withdrawn portion to be substantially directly proportional to the amount of the same gaseous component in the arterial blood of the living body.

The elongated hollow body of the cannulae preferably has a tubular portion provided with an elongated substantially flat base which extends along one side of the tubular portion for supporting the cannulae on a skin surface adjacent to the nose when each of the prongs is positioned within a corresponding nasal passage. The position of the substantially flat elongated base relative to the position and direction of the prongs is such that the support provided by this base tends to keep the cannulae in position relative to the nose. In this embodiment, the hollow tubular portion, and the base portion are preferably of substantially uniform cross-section.

The outer diameter of the base of each of the nasal prongs is substantially smaller than the inner diameter of the naris opening of the corresponding nasal passage such that the prongs do not substantially occlude the inhalation and exhalation of the living body through its nose. This may be achieved by providing nasal prongs of substantial the same shape and size wherein the cross-section of each of the prongs at its base is preferably not more than about one-half, more preferably not more than about one-third, of the cross-sectional area of the naris opening of the corresponding nasal passage in which the nasal prong is to be received.

There are several advantages to providing the cannulae as a new product wherein its hollow body comprises an elongated tube extending substantially perpendicular to the axes of the nasal prongs, and the dividing wall member comprises a septum located intermediate between the opposite ends of this main tube and extending transversely to its wall so as to divide the main tube chamber into inhalation and exhalation manifolds of approximately equal volume. One advantage is that each of the nasal prongs may extend first laterally and then curve approximately in parallel so as to fit comfortably and well within the nasal passages. Another advantage of this embodiment is that the segments of flexible tubing for connecting the inhalation manifold to a source of treating gas and the exhalation manifold to a gas analyzer may be arranged so that neither of these tubing segments passes over either the eyes or the mouth of the living body when the cannulae is properly positioned with the nasal prongs in their corresponding nasal passages.

The new product embodiment also may include a modification in which the sampling nasal prong is extended in length so as to reach a depth in its corresponding nasal passage greater than the depth reached by the other nasal prong to be used for insufflating treating gas. The extended sampling prong may reduce the likelihood that atmospheric air in the region of the naris opening will be sucked into the mouth of the prong during end-tidal sampling of exhaled breathing gas. An influx of atmospheric air into the mouth of the prong and thereby into the sampling manifold at this time may significantly reduce the accuracy of end-tidal measurements.

The invention is particularly useful for insufflating oxygen as the treating gas and for measuring carbon dioxide as the gaseous component of exhalation. When used in this fashion, the inhalation manifold is connected by a segment of flexible tubing to a source of oxygen gas, and the sampling or exhalation manifold is connected by another segment of flexible tubing to a gas analyzer, such as an infrared capnometer or a mass spectrometer, for quantitatively measuring the amount of carbon dioxide in the withdrawn portion of the exhaled breathing gas. Preferably, oxygen is fed continuously into one nasal passage via the inhalation manifold and a portion of the breathing gas is withdrawn continuously from the other nasal passage via the exhalation manifold, the peak partial pressure of measured carbon dioxide generally being considered as the end-tidal value.

BRIEF DESCRIPTION OF THE DRAWINGS

The invention may be better understood with reference to the detailed description of the preferred and other embodiments taken in conjunction with the accompanying drawings in which.

DESCRIPTION OF PREFERRED AND OTHER EMBODIMENTS

Figure 1:
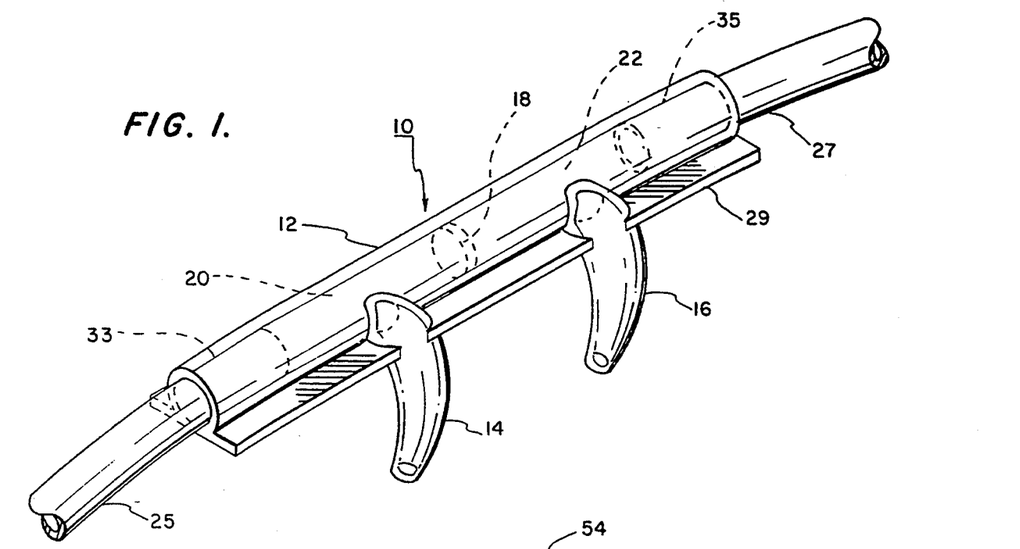
FIG. 1 is a top perspective view of a nasal cannulae according to the invention.
Figure 6:
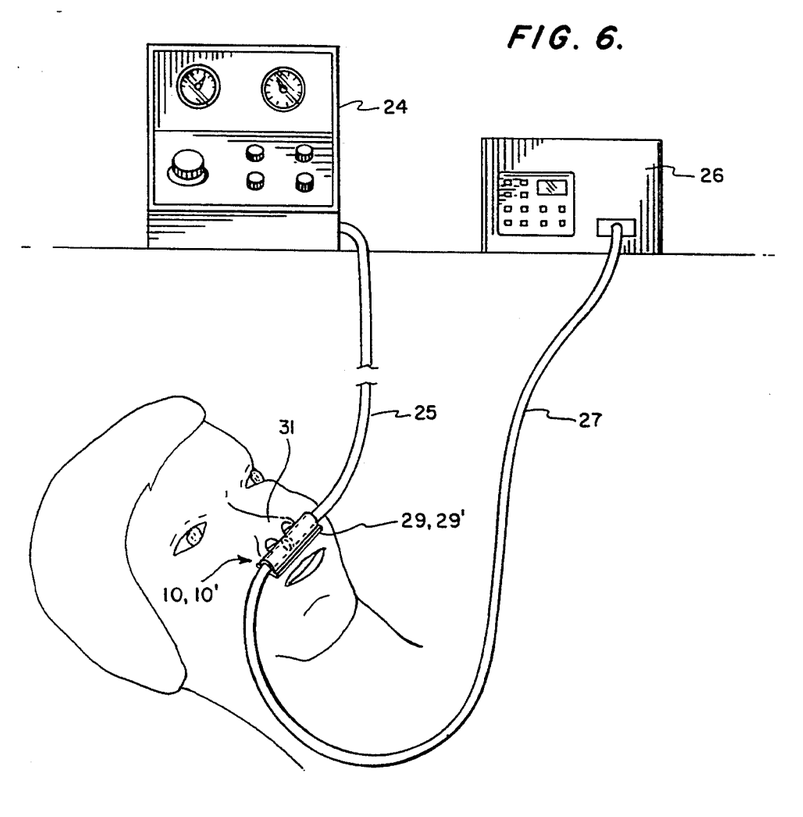
FIG. 6 is a top perspective view of the cannulae of FIG. 1 or FIG. 5 illustrating use of the cannulae with a patient and its connection to gas supply and exhalation monitoring apparatuses.

Referring to FIG. 1, there is shown a nasal cannulae, generally designated 10, having a hollow body 12 and a pair of hollow nasal prongs 14 and 16, each adapted to fit within a corresponding nasal passage of the nose of a human being as illustrated in FIG. 6. Sealingly engaging the inner surface of the interior chamber of hollow body 12 is a solid septum 18 which serves as an intermediate transverse wall dividing the interior chamber into an inhalation manifold 20 and an exhalation manifold 22.

The septum 18 is made of a substantially impermeable material and prevents fluid communication between the exhalation and inhalation manifolds. The entire cannulae 10 is preferably molded from a flexible plastic material, septum 18 being integrally molded with the wall of hollow body 12 as seen best in FIG. 5. However, septum 18 may be a separate wall member sealingly adhered to the wall of hollow body 12 by other means, such as by an adhesive composition or by fusion of the material of the septum to the material of the hollow body by solvent welding, sonic welding or the like.

Referring again to FIGS. 1 and 6, inhalation manifold 20 may be connected to an oxygen flow regulating device 24 by a segment of flexible tubing 25, and exhalation sampling manifold 22 may be connected to a breathing gas analyzer 26 via another segment of flexible tubing 27. Flexible tubing segments 25 and 27 may be obtained separately or may be supplied as part of the cannulae, in which case end portion 33 of segment 25 and the end portion 35 of segment 27 may be permanently fixed by adhesion to the corresponding end portions of cannulae body 12. The tubing ends 33 and 35 may be sealingly fixed in place by means similar to those for sealingly securing septum 18 in place within hollow body 12. On the other hand, if cannulae 10 is to be supplied without attached tubing, body 12 preferably is made of a material that is more elastic than the tubing ends 33 and 35 such that the force required for seating the ends of separately supplied tubing segments will provide air-tight sealing engagement between the respective ends and the wall of the corresponding manifold.

Cannulae 10 also may include an elongated, substantially flat base member 29 for supporting hollow body 12 on the upper lip of a patient with nasal prongs 14 and 16 positioned within the corresponding nasal passages of the patient's nose 31. The position of base member 29 relative to the position and direction of the prongs 14 and 16 is such that the support provided by base member 29 tends to keep the cannulae and its component parts in their correct position relative to nose 31 and the nasal passages therein.

In the embodiment of FIG. 1, the tubing end 33 is aligned with and received within a corresponding portion of inhalation manifold 20. Similarly, the tubing end 35 is aligned with and received within a corresponding portion of exhalation manifold 22. As seen best in the illustration of FIG. 6, this alignment of the discharge end of the oxygen supply tubing and the inlet end of the sampling tubing with the longitudinal axis of tubular body 12 has the advantage of routing both lengths of tubing so that they do not pass over either the eyes or mouth of the patient.

Figure 2:
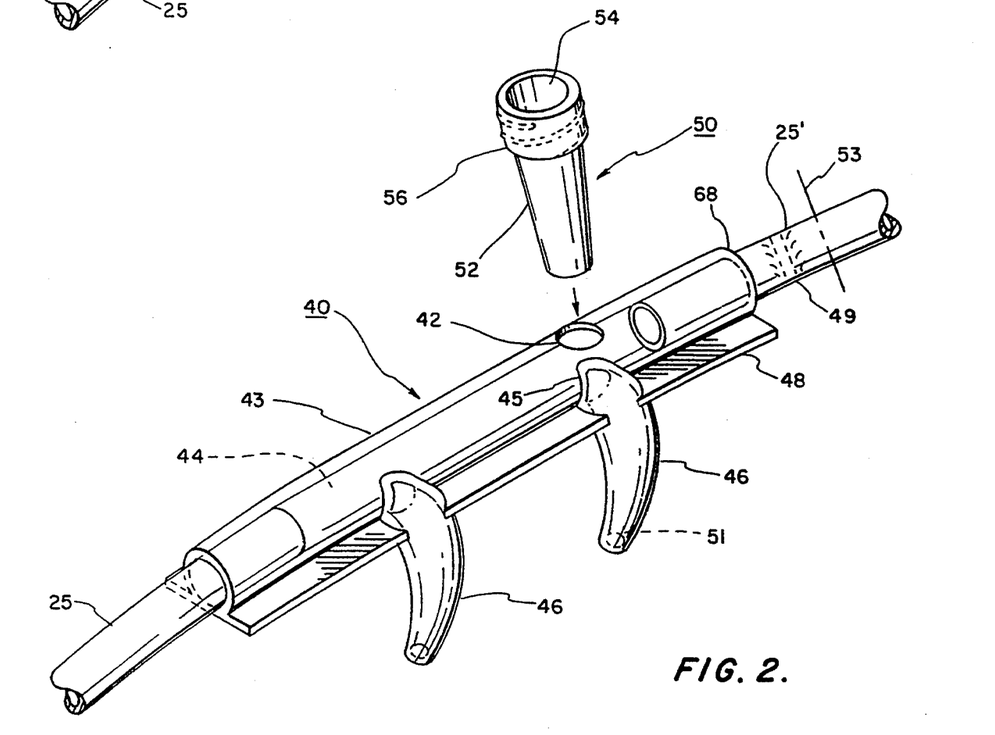
FIG. 2, FIG. 3 and FIG. 4 are top perspective views illustrating how a modified nasal cannulae according to the invention may be made from a conventional nasal cannulae.
Figures 3, 4:
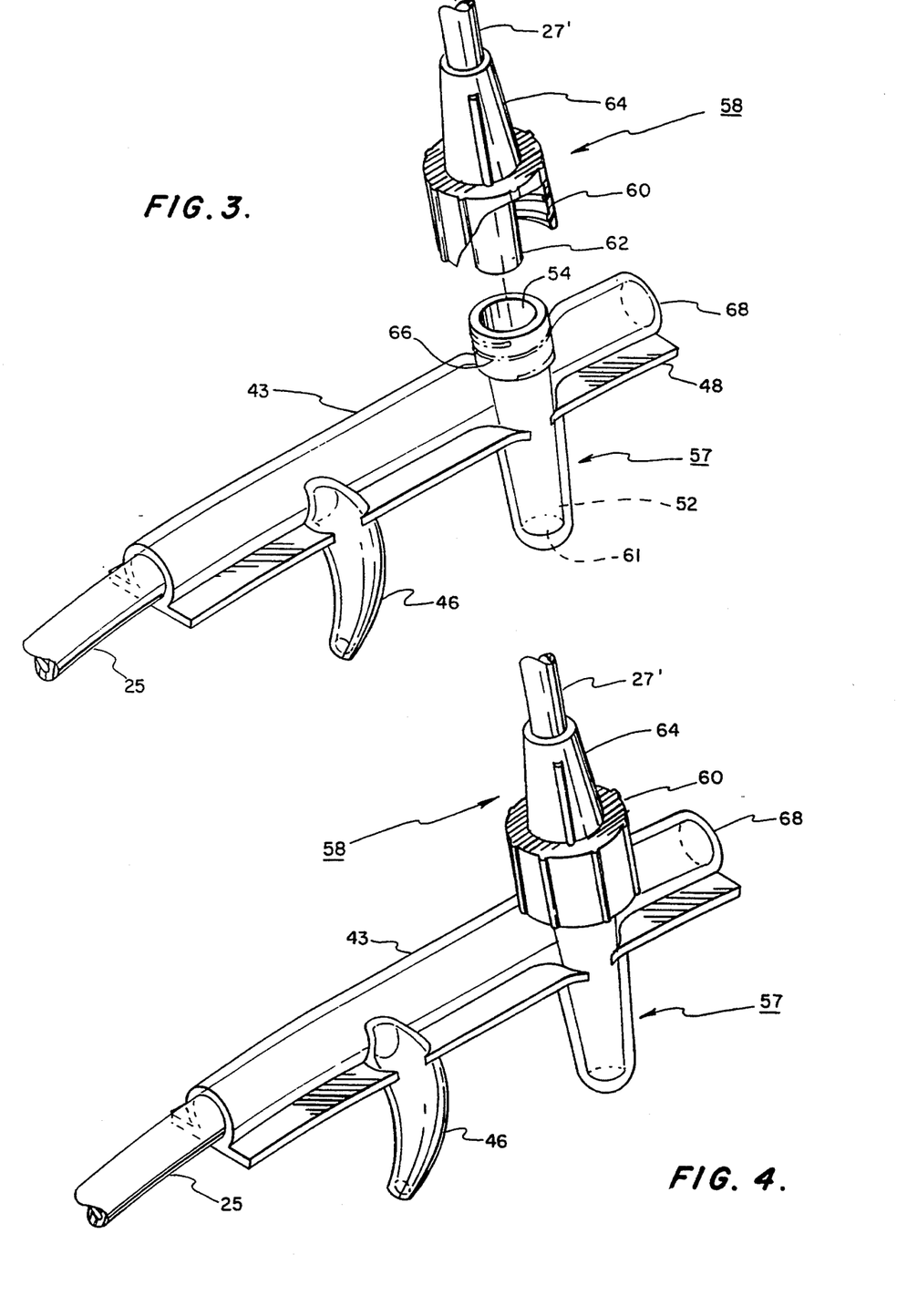

FIGS. 2-4 illustrate how a conventional nasal cannulae may be modified according to the present invention to provide a nasal cannulae which allows both oxygen administration and accurate measurements of end-tidal carbon dioxide. A conventional cannulae 40 is modified by making a small aperture 42 in the tubular main body portion 43 near the base 45 of one of the pair of prongs 46—46. A nozzle 50 may then be made by removing the tip of a syringe cap and inserting the thus altered syringe cap through aperture 42 and into the right nasal prong 46 as seen best in FIG. 3. Aperture 42 is preferably made with a needle or small cutting instrument so as to be significantly smaller than the diameter of nozzle 50 such that the rim of the aperture will sealingly engage the tapered body 52 of the nozzle. For this purpose, cannulae body 43 is preferably made of a plastic material having significant elasticity.

The portion of tapered nozzle body 52 received in the passage of prong 16 preferably has a larger external diameter than the internal diameter of the prong conduit throughout the length of the engagement between the nozzle body and the prong. This insures a gas-tight sealing engagement between the exterior surface of the nozzle and the interior surface of the prong passage to prevent fluid communication between an exhalation manifold 54 provided by the interior of the nozzle and an inhalation manifold 44 defined by cooperation between the exterior of nozzle body 52 and the wall of cannulae body 43.

Nozzle body 52 need extend into the interior of prong 46 only to the extent necessary to provide sealing engagement over a substantial portion of the length of the prong. However, it is preferred that sealing engagement between nozzle body 52 and prong 46 extend over a majority of the length of nasal prong 46, more preferably over substantially the entire length of this prong as shown in FIGS. 2-4. In fact, it may be desirable to have the nozzle body 52 extend entirely through and beyond the mouth of prong 46 so as to penetrate deeper into the nasal passage, which may help avoid contamination of the gas sampling with atmospheric air as discussed in more detail below with reference to FIG. 5. Nozzle body 52 also may have shapes other than the conical shape shown, such as having a spherical knob portion for providing sealing engagement over a substantial but intermediate portion of the length of prong 46.

Another important feature of this modification of the invention is that the material of prong 46 has substantial elasticity, and that the material of nozzle body 52 is substantially more rigid than the prong material such that the internal surface of the prong conduit will sealingly grip the external surface of nozzle body 52 when the prong material is stretched by the larger portions of the nozzle. This interaction provides a continuous gas-tight seal between the inner periphery of prong 46 and the outer periphery of nozzle body 52, much like a rubber sleeve will sealingly grip the surface of a larger article inserted therein.

As shown best in FIGS. 3 and 4, nozzle 50 has an outer flange 56 of enlarged diameter for engagement by a coupling 58 having a threaded cap 60 and a guiding hollow core 62, which is connected by a tapered transition piece 64 to a sampling line 27' and provides fluid communication between line 27' and nozzle manifold chamber 54. Because nozzle 50, cap 60 or both are preferably molded from a plastic material of some resilience, flange 56 need not have external threads in order for cap 60 to sealingly engage flange 56. However, a more secure connection may be afforded by providing flange 56 with external threads for engaging the internal threads of cap 60 as illustrated by broken lines 66 in FIGS. 2 and 3.

Body 52 of nozzle 50 also may be of a size sufficient to fully occlude the interior of cannulae 40 and alone define inhalation manifold 44 so that the usual second tubing segment 25' for infeeding oxygen to a conventional cannulae may be cut off as at 68 in FIGS. 3 and 4. If nozzle body 52 does not fully occlude cannulae chamber 44, the second oxygen infeeding tubing 25' may be provided with a gas-tight seal 49 by suturing, heat sealing or the like, and then cut off beyond this seal, as at 53. As a further alternative, oxygen also may be infed through tubing 25' and around nozzle body 52.

As evident from FIGS. 2-4, location of aperture 42 near the base 45 of nasal prong 46 allows the resulting sampling probe 57 to have an inclination relative to the cannulae base 48 such that the mouth 61 of sampling probe 57 will be at about the same relative position as the corresponding mouth 51 of prong 46 before insertion of nozzle 52. This preferred location of aperture 42 is superior to an opening made opposite to the location of base 45 of nasal prong 46 because the entry of nozzle 50 from that position tends to unduly straighten prong 56 and hold it substantially parallel to cannulae base 48. This latter positioning is undesirable because it places the mouth 61 high in the nostril instead of down in the nasal passage as required for effectively withdrawing a representative sample of exhalation gas. The proper inclination of probe 57 relative to base 48 is even more critical when nozzle body 52 is sufficiently long to extend the mouth 61 of probe 57 further into the nasal passage than the mouth 51 of the unmodified nasal prong.

Figure 5:
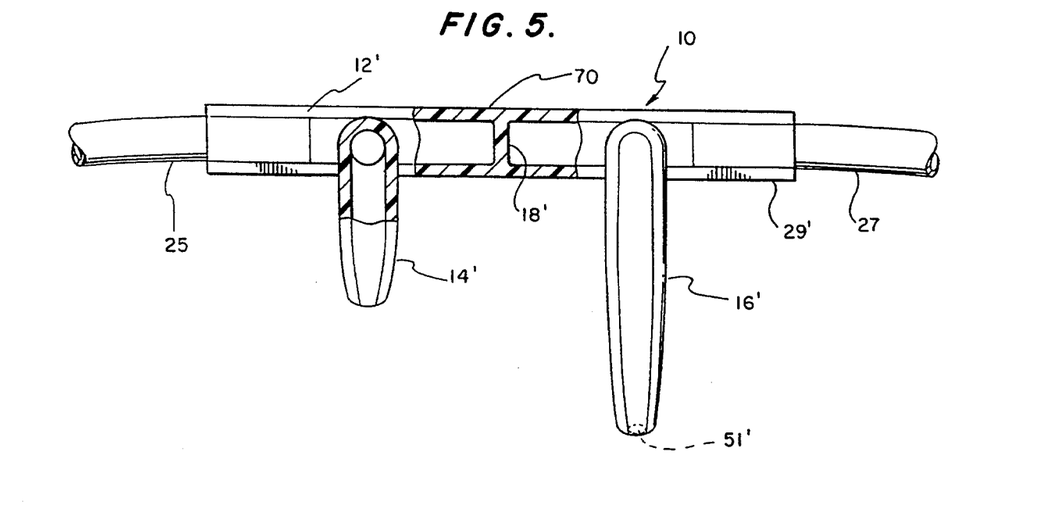
FIG. 5 is a front elevational view in partial section of a modification to the nasal cannulae of FIG. 1.

In FIG. 5, there is shown in partial section a modification of the cannulae of FIG. 1 wherein the length of sampling prong 16' has been extended relative to the length of prong 14' for administering treating gas. The amount of the extension may be any amount up to about 100%, preferably about 20 to 60%, more preferably about 50%, relative to the standard length of prong 14'. The mouth 51' of extended prong 16' is positioned to withdraw gas samples from a greater depth within the corresponding nasal passage when modified cannulae 10' is in the same position of use as cannulae 10 in FIG. 6. Withdrawing the exhalation gas sampling from a depth within the nasal passage greater than that reached by conventional nasal prongs may help to insure that this gas sample has not been diluted with atmospheric air which is always present in and around the opening of the naris. An extension greater than 100% may result in contamination of exhaled gas samples with insufflated treating gas from the central skull chamber which normally receives air from both nostrils. FIG. 5 also shows a septum 18' integrally molded with the wall 70 of tubular body 12' of cannulae 10'.

EXPERIMENTAL MEASUREMENTS AND COMPARISONS

In order to test the effectiveness of the cannulae of FIGS. 2–4, actual measurements were made by infrared capnometry to determine the end-tidal partial pressure of carbon dioxide ($P_{ET}CO_2$) in the exhaled gas of human patients in order to clinically approximate the corresponding partial pressure of arterial carbon dioxide ($P_aCO_2$). A conventional nasal cannulae (obtained from Hudson Oxygen Therapy Sales Company, Orange Park, Fla.) was modified in accordance with FIGS. 2–4 to permit the insufflation of oxygen into one nostril while monitoring exhaled gases from the other nostril. The cannulae used had a tubular body about 5 cm. in length and about 6 mm. in outside diameter and nasal prongs about 1 cm. in length and about 6 mm. in outside diameter at the base tapering to about 5 mm. outside diameter at the tip.

A nozzle 50 was created by removing the tip of a conical syringe cap which was made of relatively hard plastic and then inserting the smallest end of the cap through a small hole made at the base of one of the prongs with a relatively large needle. The tapered body portion of the syringe cap had an outside diameter of about 7.5 mm. at the base tapering to about 6 mm. outside diameter at the tip. The syringe cap was fully advanced into the nasal prong to insure sealing engagement between the outer surface of the tapered body of the cap and the inner surface of the nasal prong. The syringe cap also substantially occluded the adjacent chamber end portion 47 from the main cannulae chamber 44 so that the corresponding oxygen supply tube 25' could be cut off adjacent to cannulae end 68, if desired. However, complete occlusion of chamber end portion 47 is not necessary if oxygen supply tubing 25' is left intact because any oxygen flowing around the intermediate portion of nozzle 50 within cannulae body 43 merely enters main chamber 44 from which it is insufflated through unmodified prong 46 along with the main oxygen supply through tubing 25.

The sampling line 27' from an infrared capnometer (obtained from Allegheny International Medical Technology, St. Louis, Miss., under the name "SARACAP") was then attached to the outer flange 56 of the syringe cap by the connector 58. The tubing segments 25, 25' and 27' all had an outer diameter of about 4 mm. and were made of a plastic material harder than the plastic material of the cannulae. Calibration of the capnometer was performed according to the manufacturer's recommendations using a known sample gas containing 5% carbon dioxide, 40% nitrous oxide and 55% oxygen.

Testing was conducted with samples of exhaled gas obtained from 21 consecutive patients, ranging in age from 35 to 80 years (with a mean age of 67 years) scheduled to undergo elective cardiac surgery. The patients were transported to the operating room where oxygen administration was begun at 3 liters per minute using the nasal cannulae modified as described above. Following placement of an arterial line, blood was drawn for blood gas determination. End-tidal carbon dioxide measurements were obtained simultaneously by printing the current capnometer screen during blood sample extraction. Following induction of anesthesia, the patients were intubated with an endotracheal tube through which mechanical ventilation was then instituted. Simultaneous blood sampling and end-tidal carbon dioxide measurements were thereafter repeated. For all arterial blood samples, blood gas determinations were performed immediately using a Radiometer ABL 2 Blood Gas Analyzer, which has a self-calibrating feature occurring at regular intervals using a standard internal gas mixture.

The mean values and standard deviations were calculated for all determinations of end-tidal carbon dioxide, arterial carbon dioxide and arterial to end-tidal differences ($P_aCO_2$ - $P_{ET}CO_2$) for samples obtained via both the modified nasal cannulae and the endotracheal tube. The student's T test for paired data was used to compare arterial carbon dioxide, to end-tidal carbon dioxide, and the arterial to end-tidal differences as obtained using the modified cannulae with those as obtained using an endotracheal tube following intubation. Confidence intervals for the arterial to end-tidal differences were calculated using the T-statistic and a Pearson Product Moment Correlation Efficient was determined for arterial carbon dioxide versus end-tidal carbon dioxide for both the modified cannulae and the endotracheal tube measurements.

Figure 7:
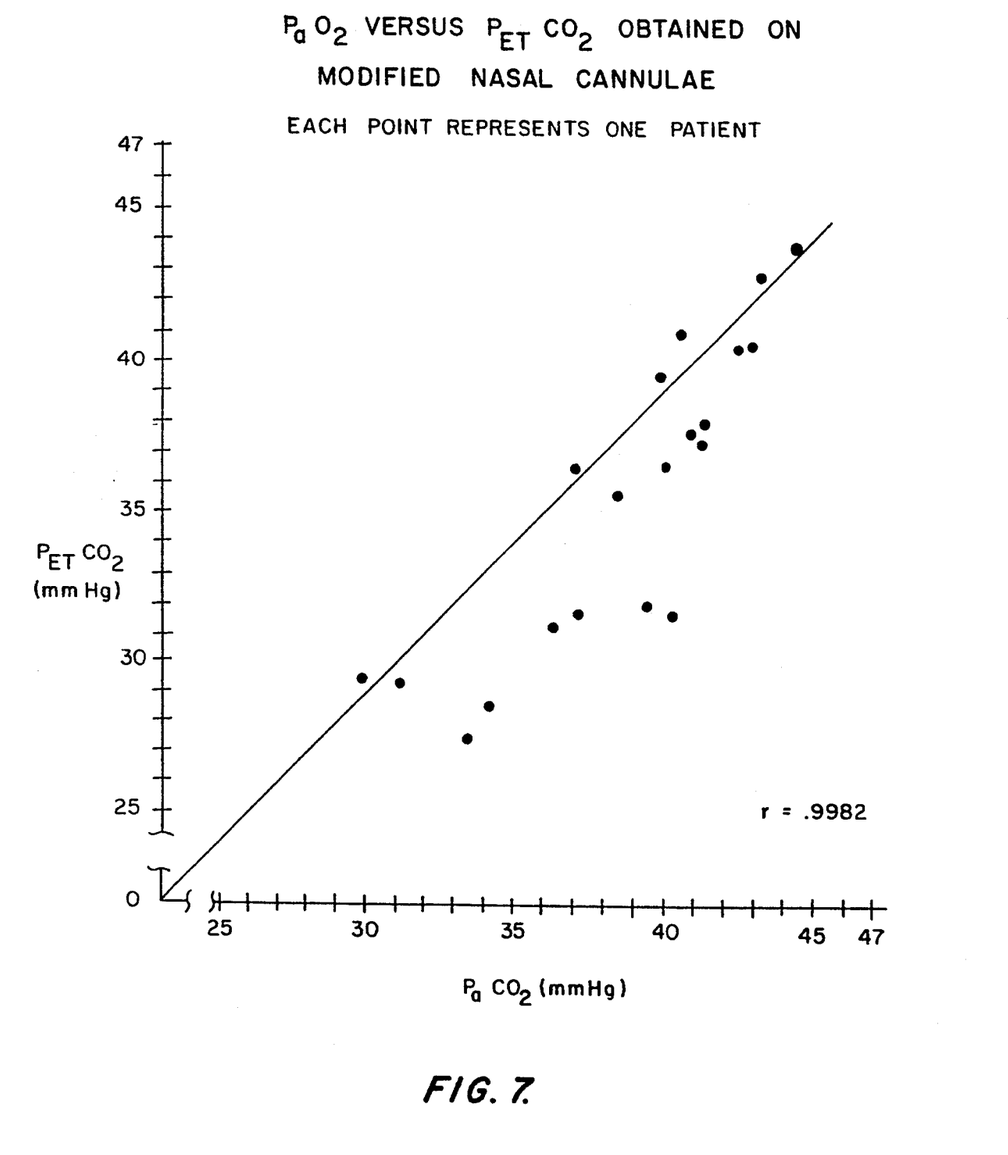
FIG. 7 is a diagram illustrating experimental data from measurements of arterial carbon dioxide versus measurements of end-tidal carbon dioxide obtained with the modified nasal cannulae of FIGS. 2–4.
Figure 8:
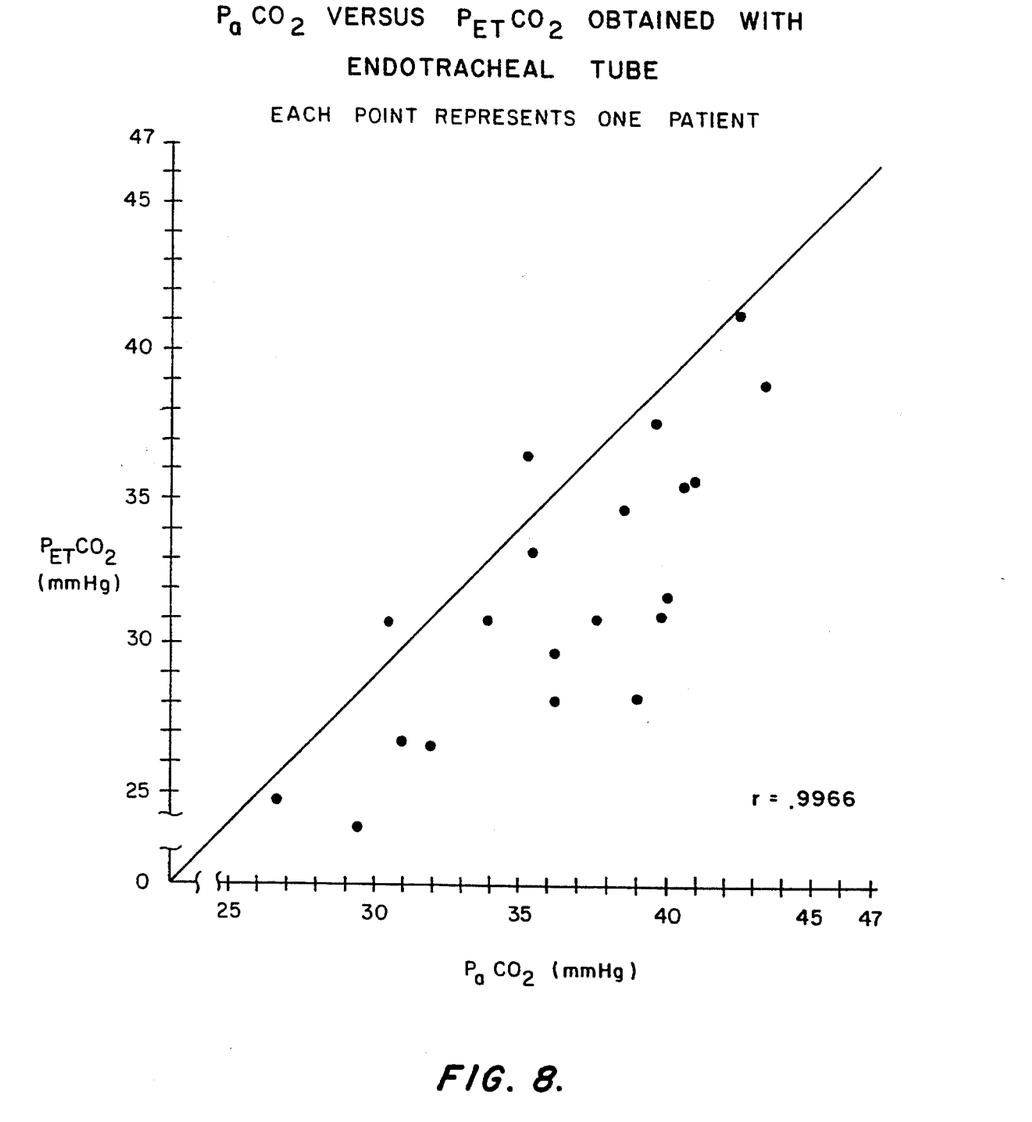
FIG. 8 is a diagram illustrating experimental data from measurements of arterial carbon dioxide versus measurements of end-tidal carbon dioxide obtained with a conventional endotracheal tube; and, FIG. 9 is a diagram illustrating a comparison between experimental data obtained with the modified nasal cannulae of FIGS. 2–4 and experimental data obtained with a conventional endotracheal tube.

The test measurements of arterial carbon dioxide versus end-tidal carbon dioxide obtained using the modified nasal cannulae of the invention on awake patients are presented in FIG. 7 and the test measurements of arterial carbon monoxide versus end-tidal carbon dioxide obtained using an endotracheal tube on anesthetized patients are presented in FIG. 8. Arterial carbon dioxide in different patients ranged from 29.9 to 44.5 mmHg. using the modified nasal cannulae to administer oxygen at a flow rate of 3 liters per minute, and from 26.5 to 44.4 mmHg. using the endotracheal tube administering 100% oxygen. End-tidal carbon dioxide in different patients ranged from 28.5 to 44.4 mmHg. using the modified nasal cannulae with an oxygen flow rate of 3 liters per minute, and from 25.8 to 45.7 mmHg. with the endotracheal tube administering 100% oxygen. The Pearson Product Moment Correlation Coefficient (r) was 0.9982 with the modified nasal cannulae and was 0.9966 with endotracheal intubation. There were no observed complications during use of either the modified nasal cannulae or the endotracheal tube.

The mean values and standard deviations for arterial carbon dioxide, end-tidal carbon dioxide and the arterial to end-tidal differences are presented in Table 1 below:

TABLE 1

|  | Nasal Cannulae | Endotracheal Tube |
|---|---|---|
| $P_aCO_2$ | 38.6 ± 3.84 | 36.8 ± 4.74 |
| $P_{ET}CO_2$ | 36.5 ± 4.68 | 33.7 ± 5.28 |
| $P_aCO_2 - P_{ET}CO_2$ | 2.1 ± 2.18 | 3.1 ± 2.80 |

Figure 9:
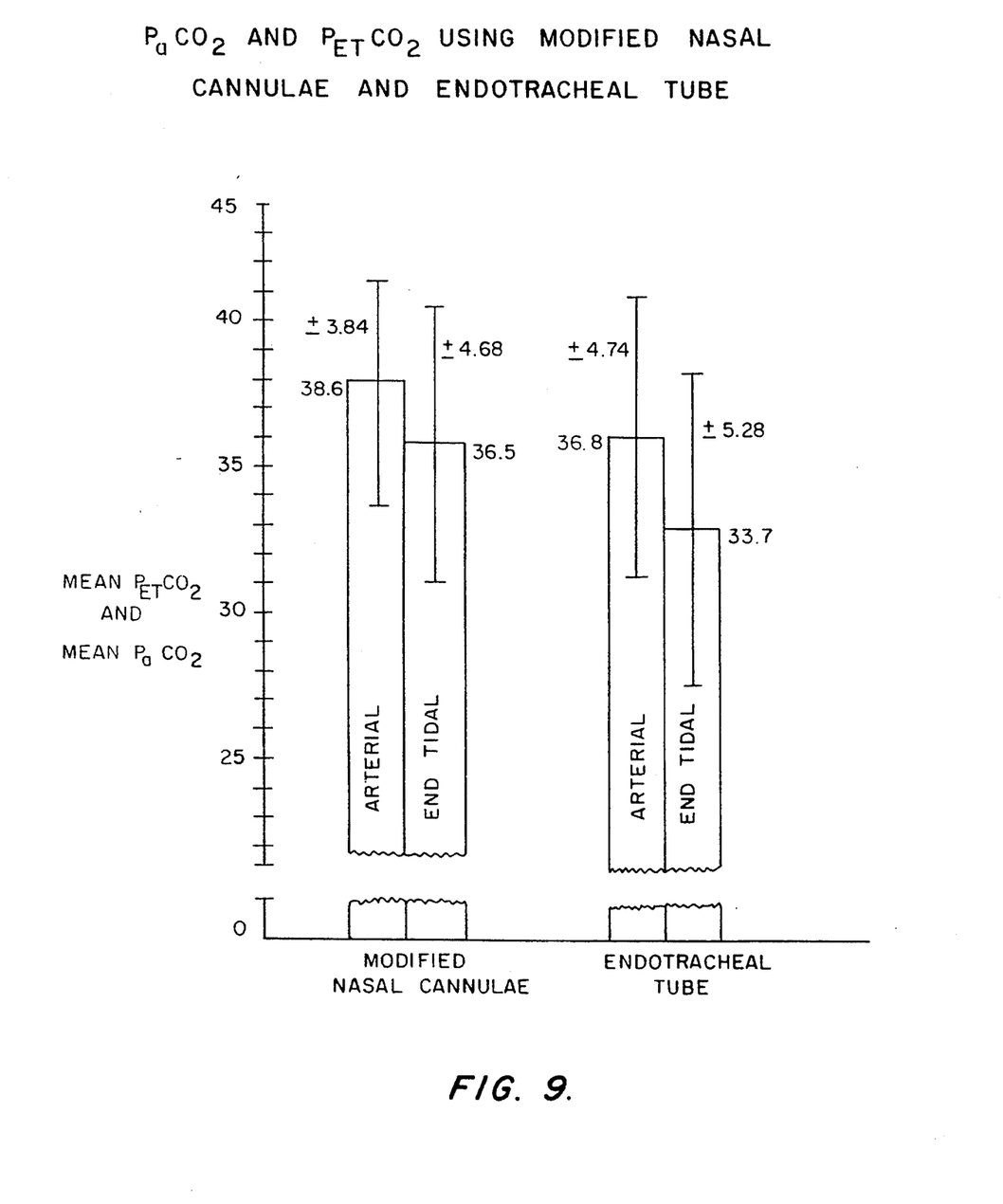

The data of Table 1 are presented graphically in FIG. 9. No medically significant differences were found between arterial carbon dioxide, end-tidal carbon dioxide, or arterial to end-tidal differences as obtained using the modified cannulae and those as obtained using the conventional endotracheal tube. On the basis of calculated confidence intervals, the arterial to end-tidal differences can be stated with 95% confidence to be between 1.09 and 3.10 using the modified nasal cannulae and between 1.78 and 4.40 using the conventional endotracheal tube.

In nineteen of twenty-one patients, no attempt was made to alter spontaneous ventilation (natural breathing). However, two patients were encountered who were predominantly mouth-breathing and this produced readings of end-tidal carbon dioxide with the modified nasal cannulae which were clearly spuriously low (15.4 and 17.8 mmHg., respectively). Since all cannulae measurements were on awake patients, these two patients were asked to breathe with their mouths closed instead of open, and this increased the end-tidal measurements to relatively normal values. Accordingly, the data derived from these two patients while breathing with their mouths closed are included in the data presented herein. Although other patients had some component of mouth breathing during cannulae sampling, significant deviations were only observed in the two patients already discussed.

The test data described above and shown in Table 1 and FIGS. 7-9 demonstrated that measurements of end-tidal carbon dioxide with the cannulae of the invention are remarkably consistent with corresponding arterial carbon dioxide measurements, and that the differences are within the previously accepted differences observed with measurements using an endotracheal tube, which prior to the present invention was believed to be the only sufficiently reliable quantitative technique while administering supplemental oxygen, other than direct arterial measurements. Thus, the mean arterial to end-tidal differences observed with the modified cannulae compare favorably with the mean arterial to end-tidal differences observed with the endotracheal tube. Accordingly, the present invention provides accurate, consistent and reproducible measurements of the quantities of end-tidal carbon dioxide as an approximation of the actual levels of arterial carbon dioxide, and may be used for this purpose in many awake patient populations. Previously, during administration of supplemental oxygen, exhaled gas measurements of sufficient accuracy to be relied upon as an approximation of arterial gas levels had been successfully achieved only by an invasive method wherein the intubated patient first had to be intubated with an endotracheal tube while under heavy sedation or general anesthesia. In comparison, the present invention provides a non-invasive method of quantitively analyzing exhaled gases as compared to the invasive method provided by sampling from an endotracheal tube.

The availability of the present invention in combination with infrared capnography or mass spectrometry to obtain reliable measurement of a component of exhaled gases during supplemental oxygen administration thus provides a new methodology for non-invasive monitoring of the respiratory status of living bodies, particularly human beings and warm-blooded animals. The present invention is believed to afford better patient management for those individuals recovering from general anesthesia and those undergoing a variety of procedures as awake patients under local or regional anesthesia. The present invention is particularly advantageous for use during relatively short-term regional procedures, such as cataract surgery. It is also believed that the invention is appropriate for use in longer term settings, such as for monitoring awake patients in an intensive care unit.

In using the invention, it is important to be cognizant of factors which may affect the accuracy of monitoring end-tidal carbon dioxide. For example, accurate monitoring of end-tidal carbon dioxide in one nostril while insufflating oxygen into the other nostril requires the presence of an intact nasal septum. This is because the present invention relies on the nasal septum to isolate the insufflated oxygen from the exhaled gases. It is believed that a perforated nasal septum may allow sufficient mixing of insufflated oxygen with exhaled gases to give spuriously low end-tidal carbon dioxide measurements, which in turn would produce an unacceptably large arterial to end-tidal difference. In addition, obstruction of the nose or sampling line with bodily secretions may lead to spuriously low measurements. Another source of potential error is the occurrence of predominantly mouth breathing as previously discussed. Certain pathological conditions, such as pulmonary embolism, also may increase the differences between end-tidal and arterial measurements, regardless of the sampling device used.

It also should be recognized that administration of a given flow of oxygen through one nostril instead of two may have a greater drying effect on the single nostril to which oxygen is delivered. Thus, the amount of oxygen which can be successfully delivered for a long period of time through one nostril may be substantially less than that which could be delivered through two nostrils. For example, the administration of 3 liters per minute of oxygen through one nostril will have a drying effect on that nostril equivalent to the administration of 6 liters per minute through both nostrils. Thus, the quantity of oxygen that can be delivered to the patient is limited to the amount that can be fed through one nostril without undue crusting of nasal secretions and/or undue drying of nasal mucosa.

What is claimed is:

1. An apparatus for insufflating a treating gas into the nose of a patient and measuring carbon dioxide content in the exhalation of the patient, said apparatus consisting of:

an elongated hollow body including a tubular portion adapted to be received on the skin surface adjacent the nose;

a wall within said hollow body defining therein both an inhalation manifold and an exhalation manifold, said wall providing a gas-tight seal positively preventing fluid communication between said inhalation and exhalation manifolds;

supply means for connecting said inhalation manifold to a supply of treating gas;

a first hollow prong in fluid communication with said inhalation manifold and adapted to be received in a first nasal passage of the nose for insufflating said treating gas into the nose;

a second hollow prong in fluid communication with said exhalation manifold and adapted to be received in a second nasal passage of the nose for withdrawing a portion of the exhalation therefrom, said prongs each being substantially smaller in diameter than the respective nasal passages, so as not to occlude said passages; and means for delivering substantially all of said withdrawn portion to a means for quantitatively measuring the amount of carbon dioxide of said withdrawn portion, the amount of said carbon dioxide in said withdrawn portion being substantially directly proportional to the amount of said carbon dioxide in the arterial blood of said patient.

2. An apparatus according to claim 1 in which the outside diameters of said nasal prongs are substantially equal and each of said prongs has a cross-sectional area which is less than about one-half of the cross-sectional area of the corresponding nasal passage in which each of said nasal prongs is adapted to be received.

3. A method for monitoring end tidal $CO_2$ in unintubated, conscious, spontaneously breathing patients who are receiving administration of local and regional anesthesia or during recovery from residual general anesthesia consisting of the steps of:

providing a nasal cannula on a patient, said cannula having an elongated hollow body; a gas-tight partition in said hollow body to divide said hollow body into a first zone and a second zone separated from each other by said gas tight partition; supply means including first conduit means communicating with said first zone and a source of oxygen, insufflation means, including second conduit means, communicating with said second zone and providing a means for detecting and measuring the partial pressure of carbon dioxide, said elongated hollow body in addition containing separate hollow nasal prongs each communicating with one of said first and second zones and with respectively each nostril of the patient;

supplying oxygen to said patient from said source of oxygen through said first conduit means to said first zone of said elongated hollow body and into the patient's nostril through one of said nasal prong means;

withdrawing carbon dioxide from said patient through the other of said nasal prongs into said second zone of said elongated hollow body, through said second conduit means and into said means for detecting and measuring the partial pressure of carbon dioxide; and determining the partial pressure of carbon dioxide at the end of the patient's exhalation to obtain a clinical approximation of the partial pressure of arterial carbon dioxide.

* * * * *